United States Patent [19]

Doyle et al.

[11] Patent Number: 5,007,434
[45] Date of Patent: Apr. 16, 1991

[54] CATHETER TIP ATTITUDE CONTROLLING GUIDE WIRE

[75] Inventors: A. Thomas Doyle, Mountain View; William S. Tremulis, Redwood City; Colleen L. McQueen, Santa Clara, all of Calif.

[73] Assignee: Advanced Cardiovascular Systems, Inc., Santa Clara, Calif.

[21] Appl. No.: 307,606

[22] Filed: Feb. 7, 1989

[51] Int. Cl.$^5$ .............................................. A61B 6/00
[52] U.S. Cl. ................................... 128/772; 128/657; 604/95
[58] Field of Search ........................ 604/95, 264, 280; 128/772, 657, 656

[56] References Cited

U.S. PATENT DOCUMENTS

| | | | |
|---|---|---|---|
| 4,554,929 | 11/1985 | Sampson et al. | 128/772 |
| 4,827,941 | 5/1989 | Taylor et al. | 604/164 |
| 4,846,186 | 7/1989 | Box et al. | 128/772 |
| 4,925,445 | 5/1990 | Sakamoto et al. | 128/772 |

*Primary Examiner*—Stephen C. Pellegrino
*Attorney, Agent, or Firm*—Fulwider, Patton, Lee & Utecht

[57] ABSTRACT

A guide wire for controlling the attitude of the tip of a catheter in a vascular system. The guide wire has an elongated shaft with a portion near the distal end having one or more of a series of bends along the length of the intermediate portion of the shaft. The bends may be preferably formed in a single plane coincident with the longitudinal axis of the shaft, and the guide wire also preferably includes a helical coil extending over the intermediate portion of the shaft and conforming to the bends in the shaft. In an alternative embodiment, the curves may be formed in a plurality of planes at least one of which is coplanar with the axis of the guide wire. In operation, the attitude of the distal end of a catheter placed over the guide wire is controlled by the movement of the tip of the catheter along the series of bends in the guide wire or by longitudinal and/or rotational movement of the guide wire with the cathether, so that the direction of the tip conincides with the tangential angle of the catheter tip on the curved portion of the guide wire. In order to provide for a wide variety of angles, the degree of curvature of the series of bends in the guide wire is preferably increased toward the direction of the distal end of the guide wire.

21 Claims, 2 Drawing Sheets

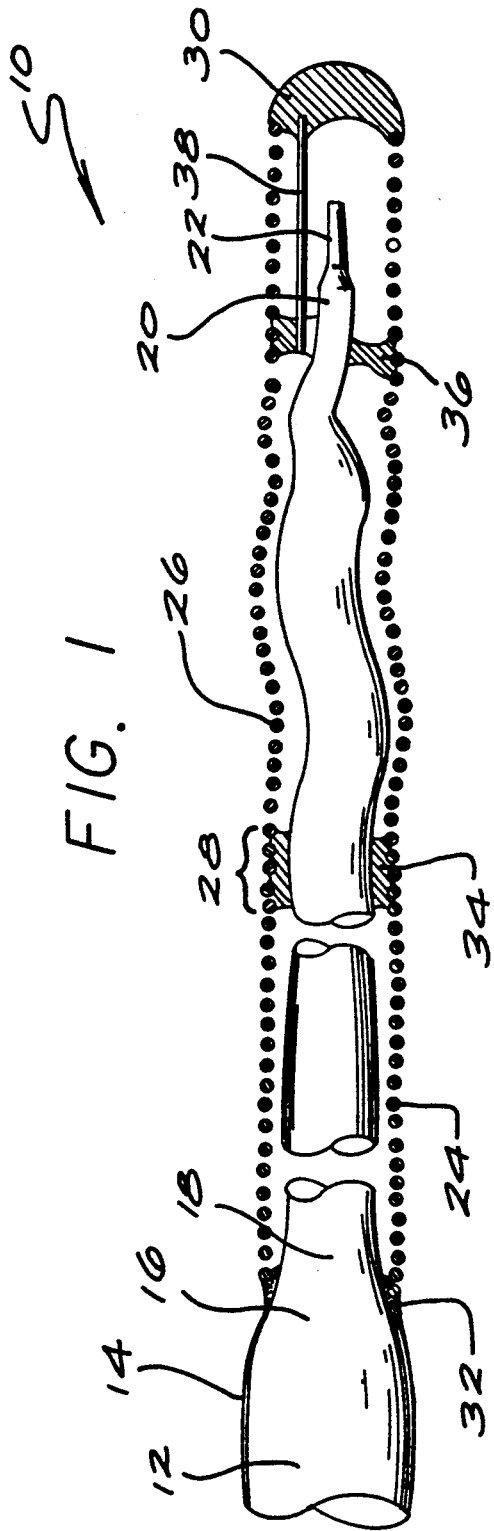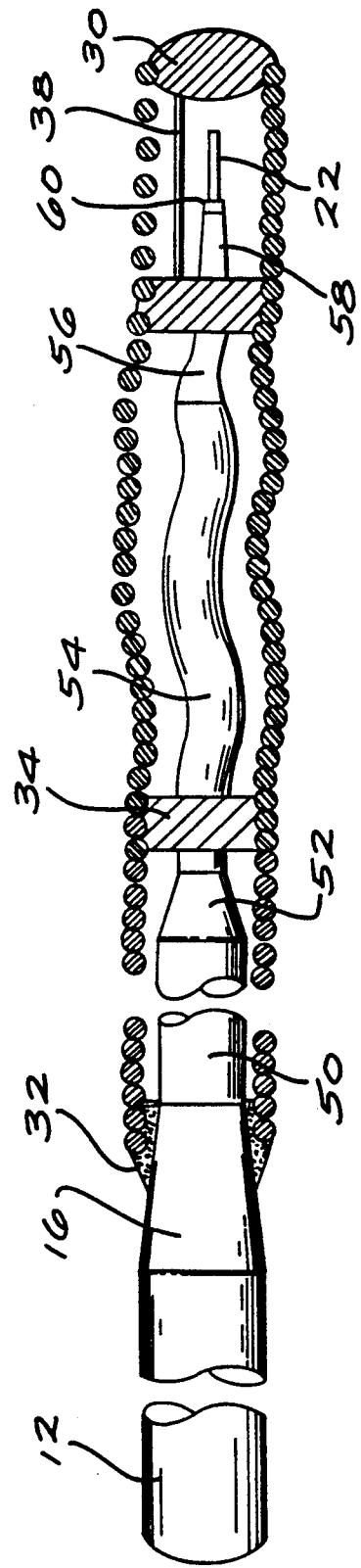

CATHETER TIP ATTITUDE CONTROLLING GUIDE WIRE

BACKGROUND OF THE INVENTION

1. Field of the Invention

This invention relates generally to catheter guide wires for in vivo use, and more particularly to a guide wire for use in controlling the angular attitude of the distal tip of a catheter adapted to pass over the guide wire.

2. Description of the Related Art

Guide wires have been used for controlling the insertion of catheters in a vascular system, or other anatomical passageways, such as for purposes of angioplasty or for insertion of angioscopes or microsensor catheters. An interventional cardiologist may form a bend at the tip of the guidewire to assist in negotiation of branches in the vascular system, and the catheter is either carried along with the guide wire as it traverses the desired path in the vascular system, or the catheter is passed over the length of the guide wire once the guide wire has been placed in the proper position. In a catheter incorporating an angioscope for viewing the internal condition of a vascular system, in which the catheter carries fiber optic bundles for both illuminating the area to be viewed and for transmitting an image back to the proximal end of the catheter for viewing, the viewing direction or attitude of the distal end of the catheter may require some control by the operator for adequate examination of the area of interest.

It has been known to provide an endoscope catheter with a plurality of inflatable balloons, spaced at intervals near the distal end of the endoscope, which are alternatively inflatable to control the direction of the tip of the endoscope. Such a system is described in U.S. Pat. No. 4,040,413. A cable pulley arrangement has also been provided for varying the degree of bending of a catheter carrying fiber optics for illumination and viewing of an area at the distal end of the catheter. The cables are attached at the appropriate points about a sheath which is disposed circumferentially around the optical fibers and the viewing bundle. Such a catheter may also include a laser optical fiber. Control of the attitude of the catheter may be changed by pulling the proximal end on one or more of the cables to cause the catheter tip to tilt or move transversely for viewing and laser irradiation of the site of interest. Such a system is described in WO83/0183. Directional control of internal imaging apparatus within a catheter may also be provided by rotation of an optical element facing at an angle within the catheter, and tilting of the angle of an element, such as a mirror, by means of cables, as is discussed in U.S. Pat. No. 4,445,892.

While many of these systems of catheter attitude control have limited ability to provide the appropriate angular orientation, they have a number of limitations in their ability to provide a wide variety of viewing angles with a mechanically simple and reliable mechanism. Therefore, it would be desirable to provide a system for varying the attitude of the distal tip of a catheter, which has a minimum of complexity embodied within the catheter in order to facilitate the construction of smaller and less obstrusive catheters. The catheter tip attitude controlling guide wire of the present invention fulfills this need.

SUMMARY OF THE INVENTION

The present invention provides a guide wire for controlling the attitude of the distal tip of a catheter adapted to be used in a vascular system or other anatomical passageways, the guide wire having an elongated shaft with a portion near the distal end having a series of bends along the length of the intermediate portion of the shaft. The distal end is generally characterized as the portion distal from the final taper in the guide wire shaft and is approximately 1.5 cm in length. The intermediate portion of the guide wire is that part which is between the tapers in the guide wire and between the distal end and the proximal shaft of the guide wire. The intermediate portion is generally approximately 28-30 cm in length and the proximal portion of the guide wire is generally in excess of 130 cm. The bends may be preferably formed in a single plane coincident with the longitudinal axis of the shaft, and the guide wire may also include a helical coil extending over a portion of the intermediate portion of the shaft and having a series of bends which conform to the bends in the shaft.

In an alternative embodiment the bends may be formed in more than one plane to assist in inducing a combination of angular motions instead of a single angular motion when the guide wire is moved axially in the catheter. In operation, the attitude of the distal end of a catheter placed over the guide wire is controlled by the movement of the tip of the catheter along the series of bends in the guide wire, so that the direction of the tip coincides with the tangential angle of the catheter tip on the curved portion of the guide wire. Alternatively, the catheter may be held stationary and the tip direction changed by moving the guide wire longitudinally within the catheter and by rotating the guide wire. In order to provide for a wide variety of angles, the degree of curvature of the series of bends in the guide wire is preferably increased toward the direction of the distal end of the guide wire.

Briefly and in general terms, a catheter tip attitude controlling guide wire according to the invention comprises an elongated shaft having a distal end, a proximal end, and an intermediate portion having a plurality of bends along a portion of the length of the intermediate portion of the shaft. The plurality of bends may preferably be formed in a single plane coincident with the longitudinal axis of the shaft; and the coil of a preferred embodiment extending over the bends in the shaft has corresponding bends. The coil may extend beyond the distal end of the shaft, and further includes a relatively smooth rounded radiopaque tip connected to the distal end of the shaft by a safety wire. At least a portion of the coil is substantially radiopaque, and a radiopaque marker is also preferably included at the proximal end of the intermediate curving portion of the shaft, to facilitate positioning of the bends in the guide wire within the catheter. The intermediate portion of the guide wire also preferably has a cross sectional diameter which decreases toward the distal end of the shaft, and the degree of curvature of the bends of the intermediate portion preferably also changes toward the distal end of the shaft.

In an alternative embodiment, the bends in the guide wire are arranged in a plurality of planes rather than a single plane, so that axial motion of the guide wire within the catheter causes a motion of the tip of the catheter representing a combination of angular motions rather than a single planar angular motion. The embodiment may provide certain advantages in controlling the altitude of some types of catheters. In other respects, the construction of the guidewire may be similar or identical to the guide wire with bends lying in a single plane.

Other aspects and advantages of the invention will become apparent from the following detailed description, and the accompanying drawings, illustrating by way of example the features of the invention.

BRIEF DESCRIPTION OF THE DRAWINGS

FIG. 1 is a enlarged, fragmentary longitudinal sectional view of a guide wire according to the invention;

FIG. 3 is an enlarged, fragmentary longitudinal sectional view of an alternative embodiment of a catheter tip attitude controlling guide wire;

DETAILED DESCRIPTION OF THE INVENTION

Figure 2A:
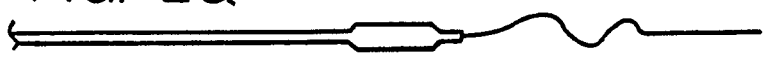
FIG. 2 is an illustration of the stages of movement of a catheter over the attitude controlling guide wire of the invention.
Figure 2B:
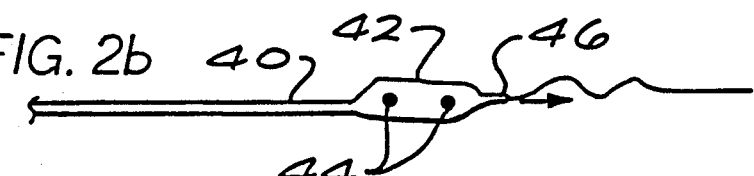
Figure 2C:
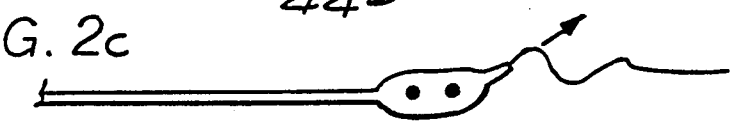
Figure 2D:
Figure 4:
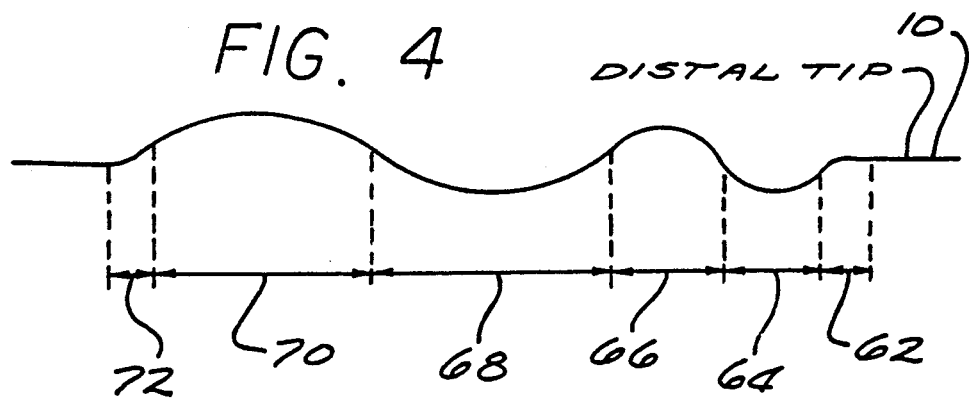
FIG. 4 is fragmentary schematic diagram of the curvature of the bends in the articulating region of the guide wire of the invention.

As is shown in the drawings, which are included for the purposes of illustration but not by way of limitation, the invention is embodied in a catheter tip attitude controlling guide wire for use with a catheter adapted to pass over the guide wire, for use in a vascular system or other anatomical passageways. The guide wire comprises an elongated shaft having a distal end, a proximal end, and an intermediate portion having a series of bends, over which the catheter can be moved to give the catheter tip a direction corresponding to the tangent of the curve of the bend. Directionally controlled catheters utilizing rotatable imaging components, cable pulley systems, or a multiplicity of lumens for controlling an array of outer balloon components for controlling attitude of the catheter tip are cumbersome and unnecessarily complex, and there is a need for a simple guide wire system readily adaptable for controlling the attitude of catheters for which directional control would be desirable, such as for an angioscope.

As is shown in FIG. 1, the guide wire 10 for controlling the direction or attitude of a catheter tip which will pass over the guide wire, for use in a vascular system, comprises a flexible cylindrical elongated shaft, typically formed from stainless steel and having a cross-sectional diameter of approximately 0.013 inches at the proximal portion at the shaft. The proximal portion of the shaft is also preferably covered with a low-friction material, such as Teflon ®, or Microglide ®. Other materials may be utilized for the shaft, such as carbon steel, titanium, Nitinol ®, or beryllium copper. The elongate wire-like cylindrical shaft can be in the form of a hollow cylindrical shaft, a helical coil wire, or a solid core wire. A solid core shaft is presently preferred. The shaft extending from the proximal portion has a tapered section 16 which decreases in cross-sectional diameter through the intermediate section 18 toward the distal end of the shaft 20, which preferably has a cross-sectional diameter of approximately 0.003 inches. Further extending from the tip of the shaft is a flattened tip portion 22, which has a cross-sectional thickness of 0.0015 inches. The intermediate section 18 typically has a cross-sectional diameter of approximately 0.007 inches.

A helical coil 24, typically formed of stainless steel to protect the elongate element 18 and for prevention of inadvertent permanent deformation of the elongate element, is secured to the tapered portion of the shaft 16 adjacent the proximal portion of the shaft at 32, typically by solder or other suitable means. An additional coil 26, which is typically formed of a material which is substantially radiopaque, such a platinum, is interleaved at the union 28 with the distal end of the stainless coil 24 and brazed or gold soldered to the intermediate portion of the shaft at this point, to both securely bond the coils together, and provide a radiopaque marker 34. The radiopaque coil is further bonded to the distal end of the shaft by solder 36, and a safety wire is additionally bonded to the distal end of the shaft at this point by the solder 36 and extending to the rounded radiopaque tip 30, which is also typically made of solder or weld.

The safety wire 38 is preferably formed of a suitable material such a tungsten, and has a thickness of approximately 0.001 inches and a width of 0.003 inches, to allow for flexibility of the extreme tip of the guide wire. The purpose of the safety wire is to prevent the loss of the distal tip 30 and the attached portion of the coil 26 in the event that the coil wire is inadvertently broken during use. The portion of the guide wire including the intermediate portion extending to the extreme distal tip is typically from 28 to 34 centimeters, and the length of the intermediate portion from the radiopaque marker 34 to the extreme distal tip is approximately 7 to 8 centimeters before curving the intermediate portion of the shaft to form the bends. The length of the guide wire from the distal soldering of the radiopaque coil and safety wire at the distal tip of the shaft, to the extreme distal end of the guide wire at the radiopaque tip is preferably between 1.5 and 1.7 centimeters. The flattened end of the distal shaft 22 is typically 0.5 centimeters and the extreme radiopaque tip typically extends another 0.5 to 0.7 centimeters beyond the distal end of the flattened tip of the shaft.

As is illustrated in FIG. 2, the directional control possible by use of the guide wire of the invention occurs as a catheter 40 is moved along over the curved portion of the guide wire 10. Alternatively, the catheter may be held stationary and the tip direction changed by moving the guidewire longitudinally within the catheter and by rotating the guide wire. Such a catheter may typically include a balloon portion 42, with radiopaque markers 44, and a distal tip 46 providing a housing for fiber optic illumination means, viewing means or laser means, which may also include a lens, or other sorts of microsensing devices such as Doppler velocity sensors. As can be seen in FIGS. 2b, 2c and 2d, as the distal tip of the catheter passes along the curved intermediate portion of the guide wire, the direction of the distal tip of the catheter corresponds to the tangential direction of the curve at that point on the guide wire, as is indicated by the arrows.

With reference to FIG. 3, a slightly modified form of the intermediate portion of the shaft may be tapered in sections. Thus, the tapered section 16 reduces the cross sectional diameter of the shaft to 0.008 inches diameter at section 50, which extends to a further tapered portion 52, narrowing down to a further reduced section having a diameter of approximately 0.007 inches, which extends to yet another tapered portion 56 extending to the 0.003 inches diameter distal portion of the shaft. A tapered portion 60 extends to the flattened extreme distal tip of the shaft 22.

The intermediate portion of the shaft, and accordingly the portion to which a helical coil is generally bonded to the shaft and following the shaft in close correspondence, typically is formed with a series of bends, which are preferably formed with an increasing degree of curvature toward the distal end of the shaft. Beginning from the distal end of the articulating portion of the guide wire, a relatively short first curved portion 62 extends typically 0.5 centimeters, extending in a plane along the longitudinal axis of the guide wire. The second curve 64, extends in a direction 180 degrees from the first curve approximately 0.9 centimeters. The third curve 66 again is a bend in the opposite direction of that of curve number 2, extending again another 0.9 centimeters. The fourth curve, 68, has approximately the same depth of curvature as the second and third curves, but is extended again the opposite direction from the third curve for approximately 1.5 centimeters, and the fifth curve 70 is similar to the fourth curve in this respect, extending again in the opposite direction from the fourth curve. The final and sixth curve 72 is similar to that of the first curve, extending a very short distance of 0.5 centimeters to the straight portion of the guide wire. All of these bends of the articulating portion of the guide wire may be formed in the same plane in the preferred mode of the invention, although it would be possible to bend the wire in the articulating portion in one or more additional planes along the length of the guide wire. In addition, portions of the articulating portion of the guide wire could be formed with a helical curvature.

Thus, the guide wire of the present invention is formed of a plurality of bends that may have different amplitudes and wavelengths. When the guide wire is moved axially within the catheter, the tip will deflect angularly in the approximate plane of the curves in the guide wire. The angle of deflection is a function of the relationship between the tip and the curves in the guide wire. The guide wire may also be rotated to rotate the catheter tip. If curves in more than one plane of the guide wire are provided, greater flexibility in the angular movement of the tip can be provided.

Also, enhanced control of rotation can be provided with a two plane orientation of the guide wire curves. Thus, the basic capabilities of the invention to provide angular control of the tip attitude may be enhanced if curves in a plurality of planes are provided. Similarly, the angular movement capabilities of the guide wire are enhanced if curves of varying amplitude and wavelength are provided. In practice, it has been found that curves with the following characteristics have been shown to be effective in controlling tip attitude for angioplasty and angioscope catheters.

|  | Distal Curve | Proximal Curve |
| --- | --- | --- |
| Amplitude | 2.2 mm | 3.4 mm |
| Wavelength | 10.0 mm | 15.0 mm |

Figure 5:
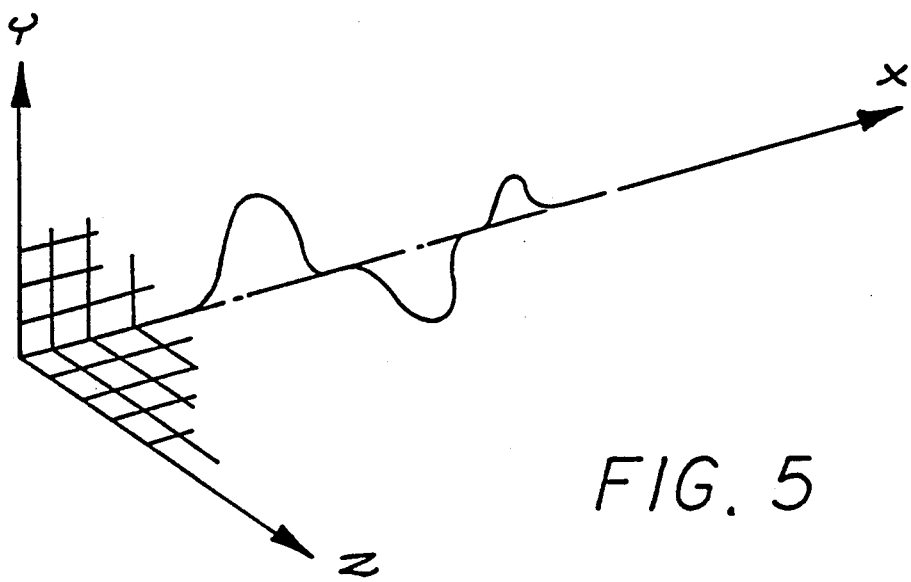
FIG. 5 is a perspective view of an alternative embodiment of the guide wire of the present invention in which the curves in the articulating region of the guide wire are formed in a plurality of planes.

FIG. 5 illustrates a perspective view of an alternative embodiment of the invention in which curves in a plurality of planes are provided. While the angles of the curves illustrated are approximately orthogonal to one another, those skilled in the art will appreciate that various combinations of numbers of curves and angles of planes may provide benefits for a specific application. In the event that the benefits of a multiplanar configuration are unnecessary, the invention may be simply and economically formed in a single plane and still provide important benefits in the control of catheter tip articulation.

Although one specific embodiment of the invention has been described and illustrated, it is clear that it is susceptible to numerous modifications and embodiments within the ability of those skilled in the art and without the exercise of the inventive faculty. Thus, it should be understood that various changes in form, detail and application of the present invention may be made without departing from the spirit and scope of this invention.

What is claimed is:

1. A guidewire which is adapted to control the attitude of the distal tip of a catheter slidably mounted thereover comprising:
   (a) an elongated shaft having a proximal portion, a distal portion with a distal tip and an intermediate portion between the proximal and distal portions; and
   (b) the intermediate portion of the elongated shaft having a plurality of permanent bends along the length thereof spaced proximally at least 1.5 cm from the distal tip of the distal portion so that, upon the longitudinal movement of a catheter over the guidewire, the attitude of the distal tip of the catheter is thereby controlled.

2. The guide wire of claim 1, wherein the bends are formed in one plane containing the longitudinal axis of the guide wire.

3. The guide wire of claim 1, wherein a helical coil having distal and proximal ends extends over at least a portion of the intermediate portion of the shaft, the helical coil being affixed to the shaft at the ends of the coil and the helical coil having a plurality of bends conforming to the bends in the shaft.

4. The guide wire of claim 3, wherein the coil extends beyond the distal end of the shaft, and includes a relatively smooth rounded tip, and a flexible safety wire having distal and proximal ends bonded to the tip at the distal end, the proximal end of the safety wire being bonded to a distal portion of the shaft.

5. The guide wire of claim 4, wherein said tip is radiopaque.

6. The guide wire of claim 3, wherein at least a portion of the coil is substantially radiopaque.

7. The guide wire of claim 1, wherein the intermediate portion of the shaft has a cross-sectional diameter which decreases toward the distal end of the shaft.

8. The guide wire of claim 7, wherein the cross-sectional diameter of the intermediate portion of the shaft decreases distally.

9. The guide wire of claim 1, wherein the degree of curvature of the plurality of bends of the intermediate portion of the shaft generally changes toward the distal end of the shaft.

10. The guide wire of claim 1, further including a radiopaque marker at the proximal end of the intermediate portion of the shaft.

11. The guide wire of claim 1, wherein the bends are formed in a plurality of planes, at least one of which is coincidental with the axis of the guide wire.

12. The guide wire of claim 1, wherein the amplitude of the curvature of the bends changes toward the distal end of the shaft.

13. A catheter tip attitude controlling guide wire for use with a catheter adapted to pass over the guide wire, the guide wire comprising an elongated shaft having a longitudinal axis having a distal end, a proximal end, and an intermediate portion having a plurality of bends formed in a plurality of planes, at least one of which is coincidental with the axis of the guide wire along at least a portion of the length of the intermediate portion of the guide wire.

14. The guide wire of claim 13, wherein a helical coil having distal and proximal ends extends over at least a portion of the intermediate portion of the shaft, the helical coil being affixed to the shaft at the ends of the coil and the helical coil having a plurality of bends conforming to the bends in the shaft.

15. The guide wire of claim 14, wherein the coil extends beyond the distal end of the shaft, and includes a relatively smooth rounded tip, and a flexible safety wire having distal and proximal ends bonded to the tip at the distal end, the proximal end of the safety wire being bonded to a distal portion of the shaft.

16. The guide wire of claim 15, wherein said tip is radiopaque.

17. The guide wire of claim 14, wherein at least a portion of the coil is substantially radiopaque.

18. The guide wire of claim 13, wherein the intermediate portion of the shaft has a cross-sectional diameter which decreases toward the distal end of the shaft.

19. The guide wire of claim 18, wherein the cross-sectional diameter of the intermediate portion of the shaft decreases distally.

20. The guide wire of claim 13, wherein the degree of curvature of the plurality of bends of the intermediate portion of the shaft generally changes toward the distal end of the shaft.

21. The guide wire of claim 13, further including a radiopaque marker at the proximal end of the intermediate portion of the shaft.

* * * * *